US012673147B2

(12) United States Patent
Ducoroy

(10) Patent No.: US 12,673,147 B2
(45) Date of Patent: Jul. 7, 2026

(54) UNIT FOR FILTERING LEUKOCYTES WITH REDUCED PLATELET ADHESION

(71) Applicant: MACO PHARMA, Mouvaux (FR)

(72) Inventor: Laurent Ducoroy, Quesnoy-sur-Deule (FR)

(73) Assignee: Maco Pharma, Mouvaux (FR)

( * ) Notice: Subject to any disclaimer, the term of this patent is extended or adjusted under 35 U.S.C. 154(b) by 339 days.

(21) Appl. No.: 18/268,534

(22) PCT Filed: Dec. 17, 2021

(86) PCT No.: PCT/EP2021/086371
§ 371 (c)(1),
(2) Date: Jun. 20, 2023

(87) PCT Pub. No.: WO2022/136138
PCT Pub. Date: Jun. 30, 2022

(65) Prior Publication Data

US 2024/0307598 A1 Sep. 19, 2024

(30) Foreign Application Priority Data

Dec. 22, 2020 (FR) ....................................... 2013941

(51) Int. Cl.
*B01D 15/10* (2006.01)
*A61M 1/02* (2006.01)
(Continued)

(52) U.S. Cl.
CPC ........ *A61M 1/3633* (2013.01); *A61M 1/0218* (2014.02); *A61M 1/0281* (2013.01);
(Continued)

(58) Field of Classification Search
CPC .............. A61M 1/0218; A61M 1/0281; A61M 1/3633; A61M 1/3636; A61M 1/3679;
(Continued)

(56) References Cited

U.S. PATENT DOCUMENTS 4,936,998 A 6/1990 Nishimura et al.

FOREIGN PATENT DOCUMENTS

EP 1156067 A2 11/2001
EP 1452193 A1 9/2004
(Continued)

OTHER PUBLICATIONS

English translation of Japanese Publication No. 5-262656 A (1993).*
(Continued)

*Primary Examiner* — John Kim
(74) *Attorney, Agent, or Firm* — Harris Beach Murtha Cullina PLLC

(57) ABSTRACT

The invention relates to a filtration unit for enabling the selective leucocytapheresis of a fluid containing blood platelets. The filtration unit includes an external pouch provided with an inlet orifice and an outlet orifice, the pouch enclosing a porous element interposed between the orifices. The porous element encloses a leucocytapheresis medium impregnated with a polymer, the polymer having the general formula -(A)m-(B)n- (I), wherein A is a unit originating from an alkoxyalkyl acrylate or alkoxyalkyl methacrylate monomer, B is a unit originating from a hydrophobic polymerisable monomer, and m and n are integers, the sum of which, m+n, is equal to 100, m being an integer greater than 80.

17 Claims, 2 Drawing Sheets

(51) Int. Cl.
*A61M 1/36* (2006.01)
*B01D 39/16* (2006.01)

(52) U.S. Cl.
CPC ........ *A61M 1/3636* (2014.02); *A61M 1/3679* (2013.01); *B01D 15/10* (2013.01); *B01D 39/1623* (2013.01); *A61M 2202/0439* (2013.01); *A61M 2207/00* (2013.01); *B01D 2239/0464* (2013.01); *B01D 2239/0618* (2013.01); *B01D 2239/10* (2013.01); *B01D 2239/1216* (2013.01); *B01D 2239/1233* (2013.01)

(58) Field of Classification Search
CPC ...... A61M 2202/0439; A61M 2207/00; B01D 15/10; B01D 39/1623; B01D 2239/0464; B01D 2239/0618; B01D 2239/10; B01D 2239/1216; B01D 2239/1233
See application file for complete search history.

(56) References Cited

FOREIGN PATENT DOCUMENTS

| | | | |
|---|---|---|---|
| EP | 2783717 | A1 | 10/2014 |
| JP | H05262656 | A | 10/1993 |

OTHER PUBLICATIONS

International Search Report issued in corresponding application No. PCT/EP2021/086371 dated Mar. 22, 2022.

* cited by examiner

[Fig. 1]
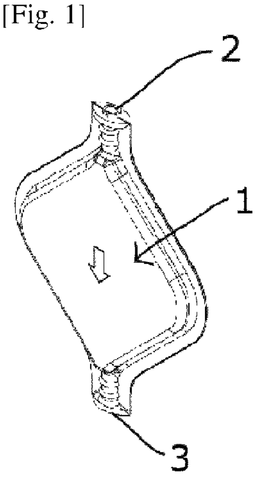
[Fig. 2]
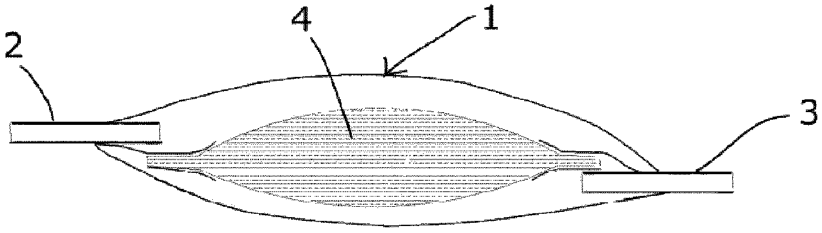
[Fig. 3]
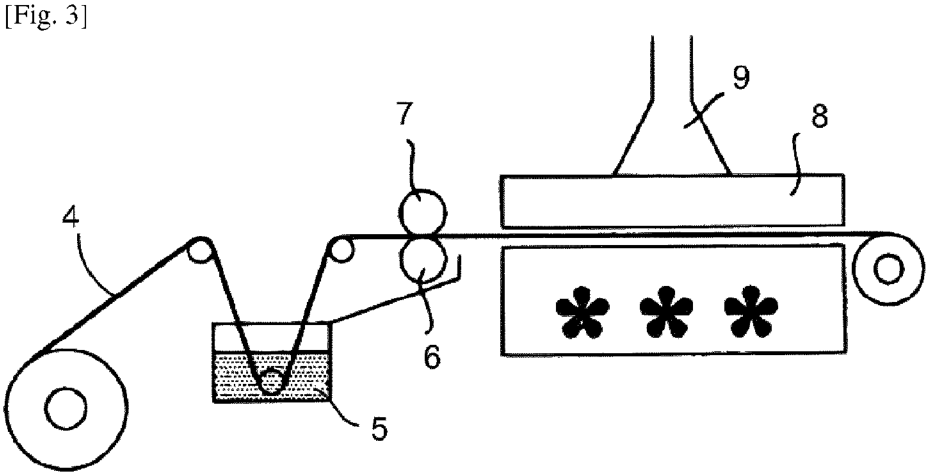

[Fig. 4]
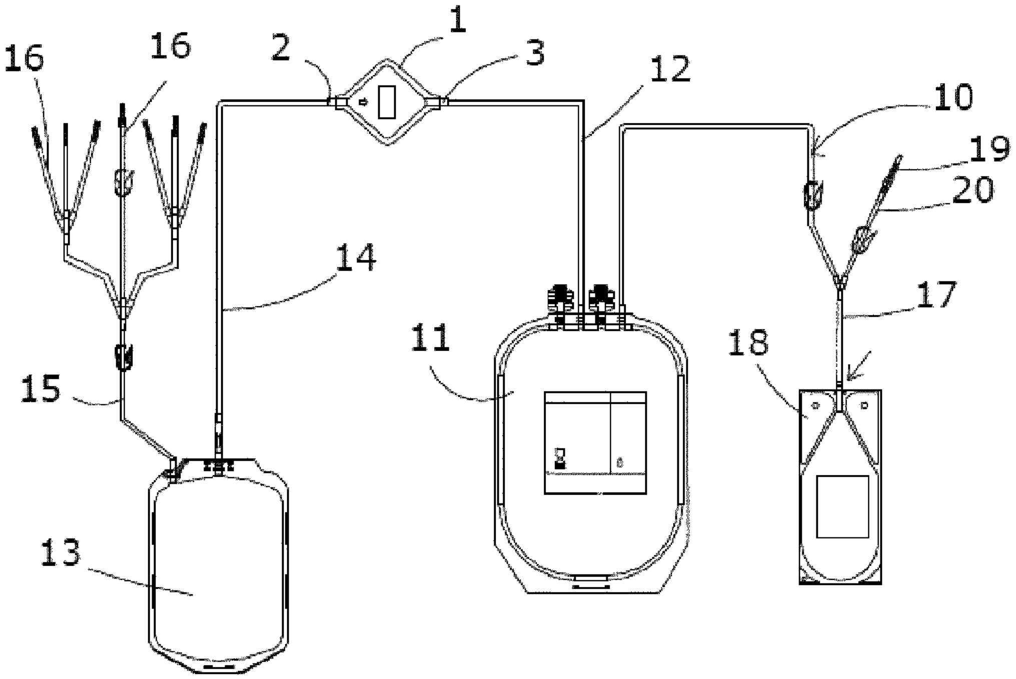
[Fig. 5]
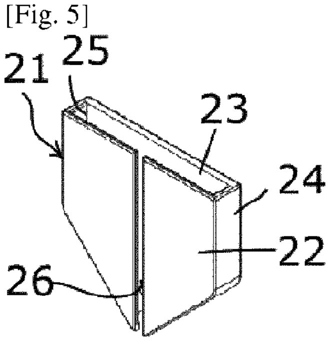
[Fig. 6]
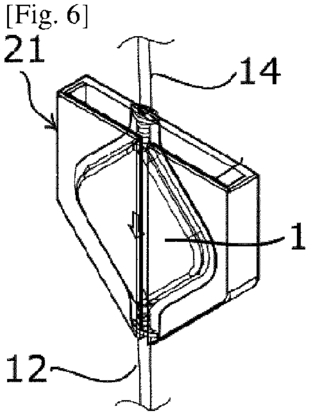

UNIT FOR FILTERING LEUKOCYTES WITH REDUCED PLATELET ADHESION

CROSS REFERENCE TO RELATED APPLICATIONS

The instant application is a U.S. National Stage application of and claims priority to PCT/EP2021/086371, filed on Dec. 17, 2021, which is a PCT application of and claims priority to French Application No. FR 2013941, filed on Dec. 22, 2020, the subject matter of both aforementioned applications are hereby incorporated by reference in their entireties.

TECHNICAL FIELD

The invention relates to a filtration unit designed to allow the selective leukodepletion of a fluid containing blood platelets, and to a bag system comprising such a unit.

BACKGROUND

The invention typically applies to the filtration of blood or a blood component containing platelets, such as platelet-rich plasma (PRP), a unitary platelet concentrate (UPC) or a platelet concentrate (PC) pool.

Whole blood is made up of two types of components: blood cells, comprising red blood cells, white blood cells and platelets, and plasma, a pale yellow liquid in which the blood cells are suspended.

At present, patients are transfused only with the blood components that are necessary for their condition. For example, only platelet concentrates are transfused to patients with thrombocytopenia, i.e. reduced platelet content in the blood.

Leukocytes have been shown to have very significant undesirable effects, which has led to efforts to eliminate them from blood components intended for transfusion. Leukocytes increase the risk of immune rejection, such as graft-versus-host disease, and promote the transmission of infectious agents. Leukocytes have also been shown to adversely affect platelet conservation.

Filtration units containing a leukodepletion medium are already known for removing leukocytes from blood components intended for transfusion. In such units, the leukodepletion medium comprises one or more membrane(s) and/or one or more non-woven layer(s) made of a polymer material and treated so as to improve the leukodepletion rate, the recovery of blood components, the filtration start-up time and/or the selectivity of filtration, for example by allowing platelets to pass through.

To eliminate leukocytes while allowing platelets to pass through, several polymer surface treatments for leukodepletion media have already been proposed.

For example, U.S. Pat. No. 4,936,998 describes a filter medium for selectively removing leukocytes. The filter medium consists of fibres coated with a polymer containing non-ionic hydrophilic groups and nitrogen-containing basic functional groups. One particular polymer is a copolymer of hydroxyethyl methacrylate and diethylaminoethyl methacrylate.

EP-2 783 717 also discloses a filter for the selective leukodepletion of a fluid comprising platelets, said filter comprising a porous medium coated with a polymer comprising a hydrophobic main chain and a hydrophilic poly (ethylene oxide) pendant chain. For example, the polymer is obtained by copolymerisation of a poly(ethylene oxide) methacrylate macromonomer and a methyl methacrylate monomer.

Another filter for removing leukocytes is disclosed in US 2006/0207937. The filter comprises a hydrophobic support material and a polymeric coating material obtained by polyreaction of a mixture of hydrophobic and hydrophilic monomers, such as a mixture of vinyl acetate and vinyl pyrrolidone. The mixture comprises between 60 and 99% hydrophobic monomer.

EP-1 452 193 also provides a filter for selectively removing leukocytes while minimising platelet loss, said filter comprising a polymer obtained from: (i) a hydroxyalkyl (meth)acrylate, (ii) a monomer containing basic nitrogen groups and (iii) a monomer comprising ethylene oxide chains containing between 2 and 9 ethylene oxide repeats. The weight-average molecular weight of the polymer is greater than 100,000 to avoid elution problems.

Document JP H05 262656 discloses a filter for selectively removing leukocytes from a platelet component, the surface of said filter being coated with an alkoxyalkyl (meth) acrylate polymer. The alkoxyalkyl (meth)acrylate may be copolymerised with an alkyl (meth)acrylate monomer. In the examples, a porous polyurethane membrane is grafted with a methoxyethyl acrylate polymer or methoxybutyl acrylate polymer.

Lastly, EP 1 156 067 proposes a filter material capable of removing leukocytes and platelets from blood while allowing red blood cells to pass through. This filter material is coated with a copolymer consisting of an alkoxyalkyl (meth) acrylate monomer and a monomer having a basic functional group such as an aminoalkyl (meth)acrylate or an aminoalkyl (meth)acrylamide.

The applicant has developed a filter material coated with a copolymer consisting of an alkoxyalkyl (meth)acrylate monomer, but which, unlike the filter material in EP 1 156 067, is capable of retaining leukocytes while allowing platelets to pass through.

SUMMARY

According to a first aspect, the invention proposes a filtration unit intended to permit the selective leukodepletion of a fluid containing blood platelets, comprising an outer housing provided with at least one inlet port and at least one outlet port, the housing enclosing a porous element interposed between said ports, said porous element enclosing a leukodepletion medium impregnated with a polymer, said polymer having the general formula $-(A)m-(B)n-$ (I), in which A is a unit derived from an alkoxyalkyl acrylate or methacrylate monomer, B is a unit derived from a hydrophobic polymerisable monomer, and m and n are integers of which the sum m+n is equal to 100, m being an integer greater than 80.

According to a second aspect, the invention relates to a bag system for leukodepletion of a fluid containing blood platelets, comprising:

- a filtration unit according to the first aspect of the invention, and
- a bag for collecting the filtrate, said bag being connected, by means of tubes, to an outlet port of the filtration unit.

According to a third aspect, the invention relates to an assembly comprising a bag system according to the second aspect of the invention, in which the filtration unit comprises a flexible housing and a rigid case intended to contain said filtration unit, said case being configured to prevent the filtration unit from swelling during the filtration.

BRIEF DESCRIPTION OF THE DRAWINGS

The appended drawings illustrate the invention:

FIG. 1 shows a schematic view of a filtration unit according to the invention.

FIG. 2 shows a schematic cross-sectional view of a filtration unit as per FIG. 1.

FIG. 3 shows a schematic view of a device for impregnating a leukodepletion medium using the pad-dry-cure principle.

FIG. 4 shows a schematic view of a bag system according to the invention.

FIG. 5 shows a schematic view of a case for the filtration unit of FIG. 1.

FIG. 6 shows a schematic view of the case in FIG. 5 containing the filtration unit in FIG. 1.

DETAILED DESCRIPTION

The invention proposes a filtration unit intended for the selective leukodepletion of a fluid containing blood platelets.

A platelet-containing fluid is, for example, whole blood, platelet-rich plasma (PRP), a unitary platelet concentrate (UPC) or a platelet concentrate (PC) pool.

In particular, the filtration unit is designed to filter a platelet concentrate obtained by apheresis or from one or more units of whole blood.

There are several methods for preparing platelet concentrates from whole blood, including the buffy coat preparation method (European Directorate for the Quality of Medicines. Healthcare (EDQM), Council of Europe: Guide to the preparation, use and quality assurance of blood components, (2019)).

According to this preparation method, a unit of whole blood is centrifuged so as to separate the blood into three layers: a plasma supernatant layer, a buffy coat intermediate layer comprising a mixture of leukocytes, platelets, red blood cells and plasma, and a red blood cell pellet layer. The buffy coat is separated from the other layers. Between four and eight separate buffy coats are then reunited and re-suspended in plasma or a platelet additive solution such as SSP+ (Macopharma). This mixture is centrifuged again (gentle centrifugation) to obtain a layer of platelet concentrate supernatant and a layer of red blood cell pellet. The platelet concentrate is then separated and stored for up to 4 to 7 days at room temperature.

When an additive solution is used, the final platelet concentrate generally consists of platelets re-suspended in a mixture formed of plasma (20-40%) and additive solution (60-80%).

During preparation, when a pool of four to six buffy coats is used, a "single dose" platelet concentrate is obtained. When a pool of seven or eight buffy coats is used, a "double dose" platelet concentrate is obtained.

There are a variety of platelet concentrates depending on the number of buffy coats used during preparation and whether or not a platelet additive solution is present.

The advantage of the filtration unit according to the invention is that it can filter platelet concentrates of any type with results that comply with current standards in terms of platelet recovery rate and number of residual leukocytes.

The filtration unit enables selective leukodepletion, i.e. it is capable of retaining leukocytes while allowing platelets to pass through.

In particular, when the fluid to be filtered is a platelet concentrate from whole blood, the filtration unit is able to obtain a number of leukocytes in the filtered fluid which is less than $1.10^6$ and to allow at least 70% of the blood platelets to pass through. In particular, the number of platelets in the platelet concentrate after filtration is at least $2.10^{11}$ platelets.

As shown in FIGS. 1 and 2, the filtration unit 1 comprises an outer housing provided with at least one inlet port 2 and at least one outlet port 3, the housing enclosing a porous element 4 interposed between said ports 2, 3, said porous element 4 enclosing a leukodepletion medium impregnated with a polymer.

DETAILED DESCRIPTION

The outer housing of the filtration unit is flexible, rigid or semi-rigid.

The leukodepletion medium impregnated with a polymer is capable of retaining leukocytes by adsorption and/or by filtration of leukocytes present in the fluid containing the platelets. The impregnated leukodepletion medium also prevents platelets from adhering to its surface.

In a leukodepletion medium, leukocytes are retained by one and/or other of the following mechanisms. The first mechanism is the adsorption of leukocytes at the surface of the medium. Leukocytes are adsorbed onto cationic and moderately hydrophobic surfaces. The quality of adsorption also depends on the contact surface available for leukocyte adsorption. The second mechanism is sieving and depends mainly on the pore diameter of the leukodepletion medium.

On the other hand, for selective filtration, the surface of the leukodepletion medium must be sufficiently biocompatible for platelets not to adhere to its surface.

The leukodepletion medium of the filtration unit of the invention is impregnated with a polymer, said polymer having the general formula -(A)m-(B)n- (I), in which A is a unit derived from an alkoxyalkyl acrylate or alkoxyalkyl methacrylate monomer, B is a unit derived from a hydrophobic polymerisable monomer, and m and n are integers of which the sum m+n is equal to 100, m being an integer greater than 80. This polymer is also called an impregnation polymer.

This polymer has the particularity of being made up of a unit derived from an alkoxyalkyl (meth)acrylate monomer, in particular methoxyethyl acrylate, which has good biocompatible properties, i.e. platelets and also leukocytes do not adsorb at the surface.

In particular, unit A has the following structure:

[Chem. 1]

(II)

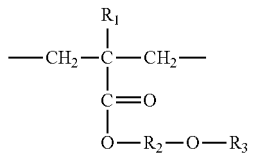

in which R1 is chosen from the group consisting of a hydrogen atom or the methyl group, R2 is a linear or branched C1-C4 alkylene bond, and R3 is a linear or branched C1-C4 alkyl group.

To promote leukocyte adhesion, the polymer also comprises a unit B derived from a hydrophobic polymerisable monomer.

Advantageously, the hydrophobic polymerisable monomer is chosen from the group consisting of an alkyl acrylate, an alkyl methacrylate and a vinyl alkylate. For example, this monomer is methyl methacrylate or vinyl acetate.

This hydrophobic monomer also helps to maintain the polymer at the surface of the leukodepletion medium.

In particular, the unit B of the impregnation polymer does not contain a basic nitrogen group. In particular, the unit B is not derived from an alkylaminoalkyl (meth)acrylate or alkylaminoalkyl acrylamide monomer.

Unit B has one of the two following structures:

[Chem. 2]

(III)

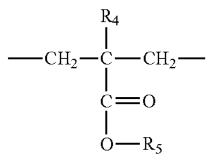

in which R4 is chosen from the group consisting of a hydrogen atom and the methyl group and R5 is a linear or branched C1-C6 alkyl group, or

[Chem. 3]

(IV)

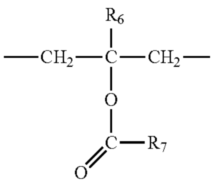

in which R6 is chosen from the group consisting of a hydrogen atom and the methyl group and R7 is a linear or branched C1-C6 alkyl group.

So as not to impair the passivation of the surfaces with respect to blood platelets, the amount of alkoxyalkyl (meth) acrylate monomer in the polymer is greater than 80 mol. %—i.e. m is greater than 80, in particular greater than 90 mol. %—i.e. m is greater than 90.

An alkoxyalkyl (meth)acrylate monomer content of less than 80 mol. % in the impregnation polymer results in a lower platelet recovery rate.

Advantageously, m is an integer less than 96 in order to retain the leukocytes sufficiently in the leukodepletion medium.

Even more advantageously, m is an integer between 90 and 96.

According to the invention, the polymer has a weight-average molar mass (Mw) of between 15,000 g/mol and 115,000 g/mol, in particular between 20,000 and 60,000 g/mol.

This polymer, which has a relatively low weight-average molar mass, contributes to better solubilisation in a solvent such as ethanol.

The weight-average molar mass is determined, for example, by steric exclusion chromatography in tetrahydrofuran with a polystyrene calibration.

The polymer has a number-average molar mass (Mn) of between 5,000 g/mol and 40,000 g/mol, in particular between 6,000 and 12,000 g/mol.

Like the weight-average molar mass, the number-average molar mass is determined, for example, by steric exclusion chromatography in tetrahydrofuran with a polystyrene calibration.

The polymolecularity index of the polymer is between 1 and 6, in particular between 1 and 5. The polymolecularity index is the ratio of the weight-average molar mass (Mw) to the number-average molar mass of the polymer (Mn). This index is used to characterise the overall dispersity of the molar masses of a polymer. An index close to 1 indicates that all the molar chains of a polymer are the same length.

The impregnation polymer thus obtained is advantageously insoluble in water, soluble in an alcoholic or ketonic solvent and resistant to steam sterilisation.

To impregnate the leukodepletion medium with the impregnation polymer, an impregnation solution is first prepared, consisting of the impregnation polymer as solute and an organic liquid as solvent.

The impregnation solution contains a low concentration of impregnation polymer. In particular, the amount of polymer dissolved in the solvent is between 1 and 10 g/L, in particular between 2 and 5 g/L.

The impregnation solvents are in particular an alcoholic solvent such as methanol or ethanol, or a ketonic solvent such as acetone or methyl ethyl ketone.

In one embodiment, impregnation is carried out according to the pad-dry-cure principle, for example using the equipment shown in FIG. 3. The leukodepletion medium 4 is soaked in the impregnation solution 5. The excess impregnated solution on the leukodepletion medium is then squeezed out by passing between two rollers 6,7 at a pressure of between 1 and 5 bar. The leukodepletion medium 4 is then conveyed into an oven 8 equipped with mechanical ventilation 9 in order to dry it by evaporation of the solvent. The speed, between 1 and 10 m/min, is regulated according to the nature and quantity of solvent carried by the leukodepletion medium.

The amount of polymer deposited on the leukodepletion medium is between 1 and 10 mg/g of leukodepletion medium, in particular between 4 and 7 mg/g of leukodepletion medium. This quantity is determined, for example, by extraction in a solvent and then by liquid phase chromatography.

In one embodiment, the leukodepletion medium comprises polyester fibres, for example polybutylene terephthalate or polyethylene terephthalate fibres.

In particular, the leukodepletion medium is formed from at least one layer of non-woven fabric. In particular, the leukodepletion medium comprises between 5 and 40 non-woven layers, and more particularly between 15 and 25 non-woven layers.

For example, the diameter of the fibres in the non-woven layer(s) is between 0.3 and 7 μm, with an average of between 1 and 3 μm.

To mechanically retain the leukocytes, the average diameter of the pores in the non-woven layer is advantageously between 3 and 15 μm, in particular between 7 and 10 μm.

With a quantity of polymer deposited on the leukodepletion medium of between 1 and 10 mg/g of leukodepletion medium, the average pore diameter and the average fibre diameter of the non-woven layer before and after impregnation remain substantially the same.

In a particular embodiment, the porous element of the filtration unit also comprises a pre-filter and/or post-filter in the form of at least one layer of non-woven fabric, which are arranged on the upstream and downstream sides of the leukodepletion medium respectively.

In particular, these pre- or post-filters have an average pore size greater than that of the leukodepletion medium, for example between 25 and 50 μm.

The pre-filters or post-filters may or may not be impregnated with a polymer to facilitate the passage of the platelets.

According to another aspect exemplified in FIG. 4, the invention relates to a bag system 10 for leukodepletion of a fluid containing blood platelets comprising: —a filtration unit 1 according to the first aspect of the invention, and a filtrate collection bag 11, said bag 11 being connected, via a tube 12, to an outlet port 3 of the filtration unit 1.

In relation to FIG. 4, a particular bag system is described for the preparation and filtration of a buffy coat pool.

The bag system 10 comprises a pool bag 13 connected or intended to be connected via a first tube 14 to the filtration unit 1 of the invention. The filtration unit 1 is connected via a second tube 12 to the filtrate collection bag 11.

For the preparation of a pool of buffy coats, the pool bag 13 is in fluid communication with a set of tubes consisting of a main tube 15 and secondary tubes 16 connected to the main tube. These secondary tubes 16 are intended to be connected in a sterile manner to at least four bags containing a buffy coat and possibly to a bag containing an additive solution for preserving platelets or plasma.

In a particular embodiment, the filtrate collection bag 11 is in fluid communication via a third tube 17 with a satellite bag 18 intended to receive the air present in the filtrate collection bag 11 and/or to collect a sample of the fluid contained in the filtrate collection bag 11.

In order to take samples of the fluid contained in the bag 11, the bag system comprises a fourth tube 20 connected to the third tube 17, said fourth tube 20 being provided at its end with a sampling means 19. The sample taken by this means is used to detect bacterial contamination (Bact/Alert® system, for example).

The tubes are fitted with clamps to control the flow of fluids inside the bag system.

When the filtration unit comprises a flexible housing, the filtration unit 1 swells during the filtration. To prevent this swelling, it is advantageous to place the filtration unit in a rigid case 21 such as that shown in FIG. 5.

The third aspect of the invention thus concerns an assembly comprising, on the one hand, a bag system 10 according to the second aspect of the invention in which the filtration unit 1 comprises a flexible housing and, on the other hand, a rigid case 21 intended to contain said filtration unit, said case being configured to prevent the filtration unit from swelling during the filtration.

Referring to FIGS. 5 and 6, this rigid case 21 comprises a cavity configured to receive the filtration unit 1.

The case 21 comprises a front wall 22 and a rear wall 23, substantially parallel to each other, and connected by two side walls 24, 25. The front wall 21 comprises a slot 26 wide enough to allow the tube 12 downstream of the filtration unit 1 to pass through, enabling the filtration unit 1 to be inserted into the case. The geometry of the case corresponds at least in part to the geometry of the filtration unit.

The case is made using 3D printing or injection moulding.

In relation to the bag system shown in FIG. 4, a particular use of the bag system 10 for the preparation of a single-dose platelet concentrate in additive solution is now described.

Between four and six bags containing a buffy coat are connected in a sterile manner, for example using a sterile connection device of the SCD type (Terumo) to the secondary tube 16 of a bag system 10. A bag of preservative solution of the SSP+ type (Macopharma, France) is also connected in a sterile manner to one of the secondary tubes 16.

The buffy coats flow into the pool bag 13. The bags containing said buffy coats are then rinsed with the preservative solution. The rest of the preservative solution is then transferred to the pool bag 13. The set of tubes 15, 16 is then separated from the pool bag 13 by welding.

The pool bag 13 is centrifuged to obtain a sedimentary layer of red blood cells and a layer of platelet concentrate supernatant.

The pool bag 13 containing the red blood cell pellet and the platelet concentrate supernatant is then pressed, for example using a pressing device of the Macopress Smart type (Macopharma, France) in order to send the platelet concentrate into the filtrate collection bag 11 via the filtration unit 1 of the invention and to obtain a leukodepleted platelet concentrate.

During this press separation and filtration stage, the filtration unit is placed in a case 21 such as that shown in FIGS. 5 and 6 to prevent the filtration unit swelling as the fluid to be filtered passes through.

Example 1: Poly(methyl methacrylate-co-2-methoxyethyl acrylate) polymer (P1: p(MMA10-MEA90))

In a reactor with a magnetic stirrer, 7.7 g of methyl methacrylate (0.077 mol) and 117.13 g of methoxyethyl acrylate (0.9 mol) were mixed under an inert atmosphere with 305 g of tetrahydrofuran and 76 g of ethanol. The mixture was stirred under inert gas bubbling at room temperature for 20 minutes.

2.5 g of azobisisobutyronitrile (AIBN) were then added and the mixture stirred for a further 10 minutes under an inert atmosphere.

The mixture was then heated in an oil bath at 70° C. for 20 hours before the solvents were evaporated at 40° C. The polymer was then washed and dried.

The resulting polymer P1 is insoluble in water. Its number-average molar mass (Mn) is approximately 6,700 g/mol, and its polymolecularity index is 2.6. The polymer contains 10 mol. % methyl methacrylate.

Example 2: Poly(methyl methacrylate-co-2-methoxyethyl acrylate) polymer (P2: p(MMA15-MEA85))

The preparation method of example 1 was adapted to obtain a poly(methyl methacrylate-co-2-methoxyethyl acrylate) having a number-average molar mass (Mn) of approximately 5,800 g/mol and a polymolecularity index of 2.9. The polymer comprises 15 mol. % methyl methacrylate.

Example 3: Poly(vinyl acetate-co-2-methoxyethyl acrylate) polymer (P3: p(VAc9-MEA91))

647 g of ethyl methyl ketone and 163 g of absolute ethanol were mixed in a reactor under an inert atmosphere and with inert gas bubbling.

Next, 1.36 g of 2,2'-azobis(2.4-dimethylvaleronitrile), 16.7 g of vinyl acetate and 187 g of 2-methoxyethyl acrylate were added. The mixture was heated to 60° C. for 20 hours; the polymer was then purified by direct distillation or by washing with water.

The copolymer P3 obtained is insoluble in water. Its weight-average molar mass (Mw) is approximately 35,700 g/mol, and its polymolecularity index is 4.3. The polymer comprises 9 mol. % vinyl acetate.

Example 4: Poly(vinyl acetate-co-2-methoxyethyl acrylate) polymer (P4: p(VAc5-MEA95))

The same method of preparation was used to obtain a poly(vinyl acetate-co-2-methoxyethyl acrylate) with a number-average molar mass (Mn) of approximately 7,300 g/mol, a polymolecularity index of 5.3 and 5 mol. % vinyl acetate.

Example 5: Preparation of Filtration Units

Layers of non-woven polybutylene terephthalate fabric (42 g/m$^2$, average pore diameter 8.5 μm) were impregnated according to the pad-dry-cure principle described above with impregnation solutions obtained by solubilising the polymer in ethanol. The impregnation solution contains a concentration of approximately 3 to 4 g/l of impregnation polymer.

Example 6: Filtration of a Platelet Concentrate in Additive Solution-Single Dose Platelet concentrates were prepared from a pool of four buffy coats and 300 ml of SSP+ additive solution (Macopharma).

The bag containing the four buffy coats and the SSP+ solution was centrifuged to obtain a platelet concentrate supernatant.

The platelet concentrate was separated and filtered under pressure using an automatic press. The separation/filtration was stopped when the red cell pellet reached halfway down the downstream tube of the filtration unit.

The results are shown in the table below. The filtration time was less than 2 minutes.

The average platelet recovery rate was determined in relation to the amount of platelets initially present in the platelet concentrate supernatant prior to filtration. This was calculated by subtracting the number of platelets in the buffy coats from the number of platelets remaining in the red cell pellet after filtration/separation.

TABLE 1

| | Polymer | | | |
|---|---|---|---|---|
| | P1 | P2 | P3 | P4 |
| Number of layers in the filtration unit | 20 | 20 | 20 | 20 |
| Filtration number | 10 | 14 | 15 | 14 |
| Average number of platelets after filtration ($10^9$/U) | 259 ± 36 | 246 ± 29 | 249 ± 29 | 264 ± 46 |
| Average platelet recovery rate (%) | 78.1 ± 10.7 | 70.7 ± 7.4 | 77.4 ± 5.7 | 78.3 ± 7.9 |
| Average number of leukocytes after filtration ($10^6$/U) | 0.032 ± 0.036 | 0.014 ± 0.023 | 0.019 ± 0.023 | 0.022 ± 0.004 |

Example 7: Filtration of a Platelet Concentrate in Additive Solution-Double Dose Platelet concentrates were prepared from eight buffy coats and 280 ml of SSP+ solution using a bag system as shown in FIG. 3.

The filtration unit comprises a flexible housing enclosing between 18 and 24 layers of non-woven polybutylene terephthalate impregnated with the polymer P3 at a concentration of 4 g/L.

For filtration, the filtration unit is inserted into a rigid case like the one shown in FIG. 5.

Platelet concentrates were separated and filtered using an automatic press (Macopress EVO Smart, Macopharma). The separation/filtration was stopped when the red cell pellet reached halfway down the tube downstream of the filtration unit.

The results are shown in the table below. The filtration time was less than five minutes.

The average platelet recovery rate was calculated in relation to the quantity of platelets initially present in the platelet concentrate supernatant before filtration.

TABLE 2

| | Number of layers in the filtration unit | | | |
|---|---|---|---|---|
| | 18 | 20 | 22 | 24 |
| Filtration number | 5 | 5 | 5 | 5 |
| Average number of platelets after filtration ($10^9$/U) | 577 ± 46 | 575 ± 55 | 591 ± 57 | 598 ± 60 |
| Minimum platelet recovery rate (%) | 98 | 98 | 94 | 94 |
| Average number of leukocytes after filtration ($10^6$/U) | 1.14 ± 1.93 | 0.40 ± 1.33 | 0.58 ± 0.8 | 0.30 ± 0.28 |

Example 8: Filtration of a Platelet Concentrate in Plasma-Single Dose

Platelet concentrates were prepared from five buffy coats and one plasma unit using a bag system as shown in FIG. 2.

The filtration unit comprises a flexible housing enclosing 24 layers of non-woven polybutylene terephthalate impregnated with the polymer P3 at a concentration of 3.25 g/L).

For filtration under pressure, the filtration unit was inserted into a rigid case like the one shown in FIG. 5 to prevent the filtration unit from swelling.

Platelet concentrates were separated and filtered using an automatic press. The separation/filtration was stopped when the red cell pellet reached halfway down the tube downstream of the filtration unit.

The results are shown in the table below. The filtration times were less than 3 minutes.

The average platelet recovery rate was calculated in relation to the quantity of platelets initially present in the platelet concentrate supernatant before filtration.

TABLE 3

| | Filtration number 16 |
|---|---|
| Average number of platelets after filtration ($10^9$/U) | 361 ± 38 |
| Average platelet recovery rate (%) | 91.4 ± 4.1 |
| Average number of leukocytes after filtration ($10^6$/U) | 0.157 ± 0.166 |

What is claimed is:

1. A filtration unit for allowing the selective leukodepletion of a fluid containing blood platelets comprising an outer housing provided with at least one inlet port and at least one outlet port, the outer housing enclosing a porous element interposed between the ports, the porous element enclosing a leukodepletion medium impregnated with a polymer, the polymer having the general formula-(A)m-(B)n-(I), in which A is an alkoxyalkyl acrylate or an alkoxyalkyl methacrylate monomer, B is a hydrophobic polymerizable monomer, and m and n are integers of which the sum m+n is equal to 100, m being an integer greater than 80.

2. The filtration unit according to claim 1, wherein A has the following structure:

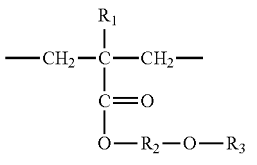

in which R1 is chosen from a group consisting of a hydrogen atom or the methyl group, R2 is a linear or branched C1-C4 alkylene bond and R3 is a linear or branched C1-C4 alkyl group.

3. The filtration unit according to claim 1, wherein A is ana methoxyethyl acrylate.

4. The filtration unit according claim 1, wherein m is an integer between 90 and 96.

5. The filtration unit according to claim 1, wherein B has one of the following two structures:

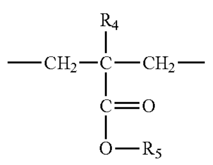

in which R4 is chosen from the group consisting of a hydrogen atom and a methyl group and R5 is a linear or branched C1-C6 alkyl group, or

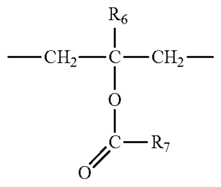

in which R6 is chosen from the group consisting of a hydrogen atom and a methyl group and R7 is a C1-C6 alkyl group.

6. The filtration unit according to claim 1, B is is one of methyl methacrylate or vinyl acetate.

7. The filtration unit according to claim 1, wherein the number-average molar mass of the polymer is between 5,000 g/mol and 40,000 g/mol.

8. The filtration unit according to claim 1, wherein the weight-average molar mass of the polymer is between 15,000 g/mol and 115,000 g/mol.

9. The filtration unit according to claim 1, wherein the polymer has a polymolecularity index of between 1 and 6.

10. The filtration unit according to claim 1, wherein the quantity of polymer deposited on the leukodepletion medium is between 1 and 10 mg/g of leukodepletion medium.

11. The filtration unit according to claim 1, wherein the leukodepletion medium comprises polybutylene terephthalate or polyethylene terephthalate fibers.

12. The filtration unit according to claim 1, wherein the leukodepletion medium is formed by at least one layer of non-woven fabric.

13. The filtration unit according to claim 12, wherein the average pore diameter of the non-woven layer is between 3 and 15 μm.

14. A system for the leukodepletion of a fluid containing blood platelets, comprising:

a filtration unit according to claim 1, and a bag for collecting the filtrate, the bag being connected by a tube to an outlet port of the filtration unit.

15. The bag system according to claim 14, in which the filtration unit comprises a flexible outer housing and a rigid case configured to contain the filtration unit and prevent the filtration unit from swelling during filtration.

16. A filtration unit for allowing the selective leukodepletion of a fluid containing blood platelets comprising an outer housing provided with at least one inlet port and at least one outlet port, the outer housing enclosing a porous element interposed between the ports, the porous element enclosing a leukodepletion medium impregnated with a polymer, the polymer having the general formula-(A)m-(B)n-(I), in which A is an alkoxyalkyl acrylate or an alkoxyalkyl methacrylate monomer, B is a hydrophobic polymerizable monomer, and m and n are integers of which the sum mtn is equal to 100, m being an integer greater than 80; and wherein B is a monomer chosen from the group consisting of an alkyl acrylate, an alkyl methacrylate and a vinyl alkylate.

17. A filtration unit for allowing the selective leukodepletion of a fluid containing blood platelets comprising an outer housing provided with at least one inlet port and at least one outlet port, the outer housing enclosing a porous element interposed between the ports, the porous element enclosing a leukodepletion medium impregnated with a polymer, the polymer having the general formula-(A)m-(B)n-(I), in which A is an alkoxyalkyl acrylate or an alkoxyalkyl methacrylate monomer, B is a hydrophobic polymerizable monomer, and m and n are integers of which the sum m+n is equal to 100, m being an integer greater than 80; and wherein B does not contain a basic nitrogen group.

* * * * *